United States Patent
Black (10) Patent No.: US 10,507,044 B2
(45) Date of Patent: Dec. 17, 2019

(54) OCCIPITAL PLATE SYSTEMS

(71) Applicant: GLOBUS MEDICAL, INC., Audubon, PA (US)

(72) Inventor: Michael E. Black, Phoenixville, PA (US)

(73) Assignee: GLOBUS MEDICAL, INC., Audubon, PA (US)

( * ) Notice: Subject to any disclaimer, the term of this patent is extended or adjusted under 35 U.S.C. 154(b) by 87 days.

(21) Appl. No.: 15/397,772

(22) Filed: Jan. 4, 2017

(65) Prior Publication Data
US 2017/0112544 A1 Apr. 27, 2017

Related U.S. Application Data (62) Division of application No. 13/417,800, filed on Mar. 12, 2012, now Pat. No. 9,566,094.

(51) Int. Cl.
*A61B 17/80* (2006.01)
*A61B 17/70* (2006.01)

(52) U.S. Cl.
CPC .......... *A61B 17/7055* (2013.01); *A61B 17/70* (2013.01); *A61B 17/7047* (2013.01); *A61B 17/7053* (2013.01); *A61B 17/7056* (2013.01); *A61B 17/7061* (2013.01)

(58) Field of Classification Search
CPC ............ A61B 17/7023; A61B 17/7055; A61B 17/7047; A61B 17/7053; A61B 17/7056; A61B 17/80; A61B 17/8019; A61B 17/8061; A61B 17/7052; A61B 17/7049; A61B 17/7041

USPC ...................... 606/246–299, 70–71
See application file for complete search history.

(56) References Cited

U.S. PATENT DOCUMENTS

| | | | |
|---|---|---|---|
| 8,900,276 B2* | 12/2014 | Purcell | A61B 17/7058 606/280 |
| 9,216,042 B2* | 12/2015 | Berrevoets | A61B 17/7055 606/264 |
| 9,232,966 B2* | 1/2016 | Refai | A61B 17/7013 606/278 |
| 2004/0153070 A1 | 8/2004 | Barker et al. | |
| 2005/0124994 A1 | 6/2005 | Berger et al. | |
| 2007/0118121 A1 | 5/2007 | Purcell et al. | |
| 2007/0233119 A1* | 10/2007 | Markworth | A61B 17/7044 606/300 |
| 2008/0051783 A1 | 2/2008 | Null et al. | |
| 2008/0125781 A1 | 5/2008 | Hoffman et al. | |
| 2010/0222779 A1 | 9/2010 | Ziemek et al. | |
| 2010/0324557 A1 | 12/2010 | Cheema et al. | |

(Continued)

*Primary Examiner* — Kevin T Truong
*Assistant Examiner* — Jessica Weiss (57) ABSTRACT

Occipital plate systems are described. The occipital plate systems include an occipital plate having an upper portion and lower portion. The lower portion can include an opening for receiving one or more lateral members therethrough. The lateral members include top and/or side apertures for receiving lateral connectors that are attached to polyaxial screw receiving members. The occipital plate systems can also include low-profile clamping arms that are operably attached to an occipital plate via an extension member and articulating joint member. The clamping arms, along with tension cables attached intermittently along its length, can be used in addition to or instead of screws and hooks to secure an occipital plate system to vertebrae.

13 Claims, 8 Drawing Sheets

(56) References Cited

U.S. PATENT DOCUMENTS

2011/0004250 A1* 1/2011 Uribe ................. A61B 17/7055
606/264
2011/0190824 A1* 8/2011 Gephart ................. A61B 17/70
606/278
2011/0251645 A1 10/2011 Black et al.

* cited by examiner

OCCIPITAL PLATE SYSTEMS

CROSS-REFERENCE TO RELATED APPLICATION

This application is a divisional of U.S. patent application Ser. No. 13/417,800, filed Mar. 12, 2012, which is hereby incorporated by reference in its entirety for all purposes.

FIELD OF THE INVENTION

The present application is generally directed to orthopedic stabilization systems, and in particular, to occipital plate systems.

BACKGROUND OF THE INVENTION

Many types of spinal irregularities cause pain, limit range of motion, or injure the nervous system within the spinal column. These irregularities can result from, without limitations, trauma, tumor, disc degeneration, and disease. Often, these irregularities are treated by immobilizing a portion of the spine. This treatment typically involves affixing a plurality of screws and/or hooks to one or more vertebrae and connecting the screws or hooks to one or more elongate rods that generally extend in the direction of the axis of the spine. Such a system of screws and rods can extend from the skull down to lower vertebral bodies.

Accordingly, there is a need for improved systems involving screws and rods for spinal stabilization.

SUMMARY OF THE INVENTION

Various occipital plate systems are provided. In some embodiments, an occipital plate system comprises an occipital plate, the occipital plate having an upper portion and a lower portion, the lower portion including at least one opening for receiving one or more lateral members.

In other embodiments, an occipital plate system comprises an occipital plate, the occipital plate having an upper portion and a lower portion, the upper portion being tapered such that a thickness of the upper portion is less than a thickness of the lower portion.

In other embodiments, an occipital plate system comprises an occipital plate having an upper portion and a lower portion, the upper portion comprising a plurality of holes for receiving one or more fasteners therethrough. The system further includes a pair of clamping arms operably attached to the occipital plate, wherein the clamping arms are capable of medial movement in order to clamp the system to vertebral bone.

BRIEF DESCRIPTION OF THE DRAWINGS

The invention will be more readily understood with reference to the embodiments thereof illustrated in the attached figures, in which.

DETAILED DESCRIPTION OF THE ILLUSTRATED EMBODIMENTS

Embodiments of the invention will now be described. The following detailed description of the invention is not intended to be illustrative of all embodiments. In describing embodiments of the present invention, specific terminology is employed for the sake of clarity. However, the invention is not intended to be limited to the specific terminology so selected. It is to be understood that each specific element includes all technical equivalents that operate in a similar manner to accomplish a similar purpose.

The present application is generally directed to orthopedic stabilization systems, and in particular, to occipital plate systems. The improved occipital plate systems can include occipital plates operably attached to one or more stabilization rods. In some embodiments, the stabilization rods extend from the skull (e.g., the occipital bone) down to the cervical, thoracic and/or lumbar vertebrae.

Figure 1:
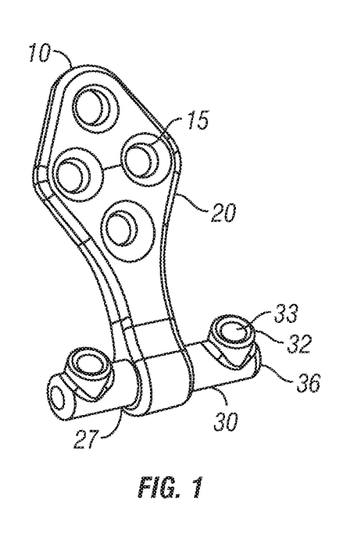
FIG. 1 is a top perspective view of an improved occipital plate according to some embodiments.
Figure 2:
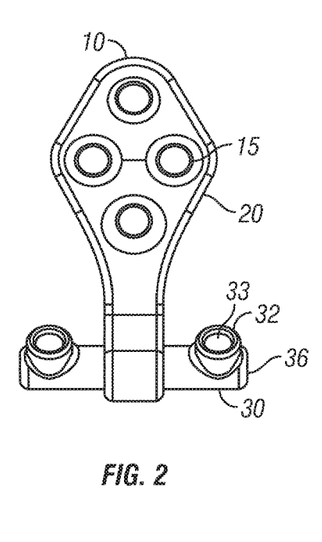
FIG. 2 is a top view of the occipital plate of FIG. 1.
Figure 3:
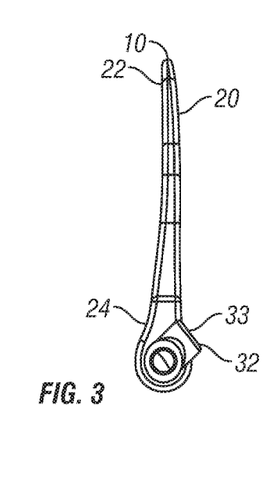
FIG. 3 is a side view of the occipital plate of FIG. 1.

FIG. 1 is a top perspective view of an improved occipital plate according to some embodiments, while FIG. 2 is a top view of the same plate. The occipital plate 10 comprises a body 20 having an upper portion 22 and a lower portion 24 (as shown in FIG. 3). Details of the plate are discussed below.

The upper portion 22 of the occipital plate 10 comprises one or more holes 15. The holes 15 are configured to receive one or more fasteners for fixing the plate 10 to a bone member, such as an occipital bone. The one or more holes 15 can be provided in a desirable pattern to assist in attachment of the plate 10 to bone. As shown in FIG. 1, the holes 15 can desirably be placed in a diamond-shaped pattern in order to receive at least four fasteners to secure the plate 10 to the occipital bone. While the diamond-shaped pattern provides for the even distribution of the holes of the fasteners, thereby providing a secure means to secure the occipital plate to a bone member, other shapes and patterns can also be used for the holes.

The upper portion 22 of the occipital plate 10 smoothly transitions into a lower portion 24. The lower portion 24 includes an opening 27 for receiving one or more lateral members 30 that can accommodate one or more rod accepting members (as best shown in FIGS. 4A-6B). As shown in FIG. 3, which illustrates a side profile of the plate 10, the plate is advantageously tapered near the upper portion 22 relative to the lower portion 24 of the plate. This tapering feature advantageously minimizes the thickness of the plate 10 near an upper portion of the plate, thereby reducing the profile of the plate in the occipital region of the skull, thus adding more comfort to the patient. In some embodiments, an upper portion 22 of the plate 10 can have a thickness that is between 20 and 80 percent of the thickness of a lower portion 24 of the plate 10.

The lower portion 24 of the plate 10 can include an opening 27 for receiving one or more lateral members 30. As shown in FIG. 1, the lateral members 30 can each include one or more receiving apertures (e.g., top apertures 32 or side apertures 36) that can receive one or more rod accepting components (e.g., polyaxial screw head receivers 100, 120 or 140 as shown in FIGS. 4A-6B). In some embodiments, the lateral members 30 are rotatable and/or translatable, such that they are adjustable prior to the locking of the members. In other embodiments, the lateral members 30 are fixed in a desirable orientation and simply receive the one or more rod accepting components without any adjustability. As shown best in FIG. 3, the top aperture 32 can have an opening 33 having a longitudinal axis that is at an angle relative to a longitudinal axis of the plate.

In some embodiments, the lower portion 24 of the plate 10 can comprise a substantially straight segment have an extended length that extends from an occipital bone towards a sub-occipital region, and in some cases, down towards a lower vertebra member (e.g., a cervical member). By having an extended length, this advantageously accommodates shorter posterior stabilization rods, thereby helping to stabilize the entire construct.

The rod accepting components can comprise a number of different members for receiving one or more stabilization rods. In some embodiments, the rod accepting components can comprise lateral connectors that extend out laterally from the side apertures 36 of the lateral members 30. The lateral connectors can hold one or more polyaxial screw head receivers to receive one or more stabilization rods. In some embodiments, the polyaxial screw head receivers are advantageously capable of rotatable and/or translatable adjustment. Variations of the lateral connectors are shown with respect to FIGS. 4A-6B.

Figure 4A:
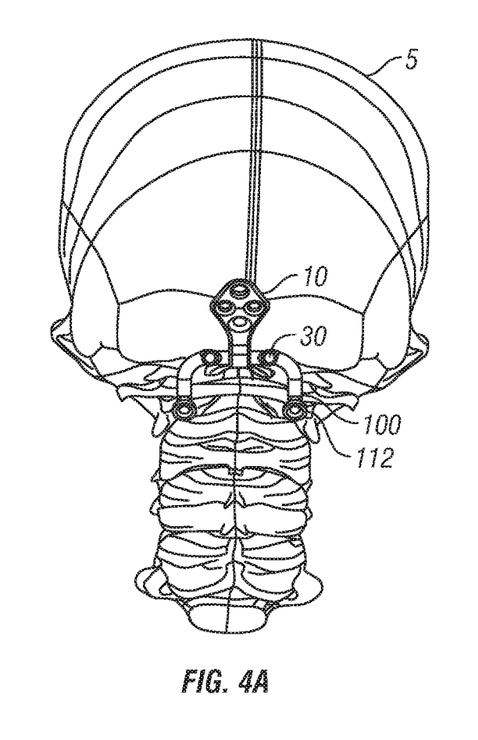
FIGS. 4A and 4B illustrate an occipital plate with lateral connectors attached thereto according to some embodiments.
Figure 4B:
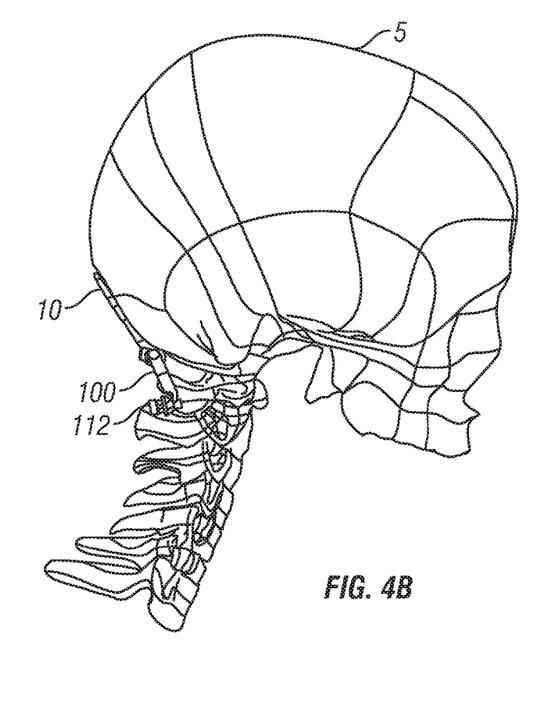

FIG. 4A and 4B illustrate an occipital plate 10 attached to occipital bone 5, the occipital plate 10 having lateral connectors 100 extending outwardly from the lateral members 30 according to some embodiments. The lateral connectors 100 operably extend outwardly from the lateral members 30. As shown in FIGS. 4A and 4B, the lateral connectors 100 each comprise an arm that extends outwardly and curves downward. The bottom ends of the lateral connectors 100 include one or more polyaxial screw head receivers 112 for receiving a rod member. As the lateral connectors 100 curve downwardly and extend past a sub-occipital region and toward the vertebrae (e.g., the cervical region), this advantageously reduces the need to extend one or more stabilization rods up into the occiput region.

Figure 5A:
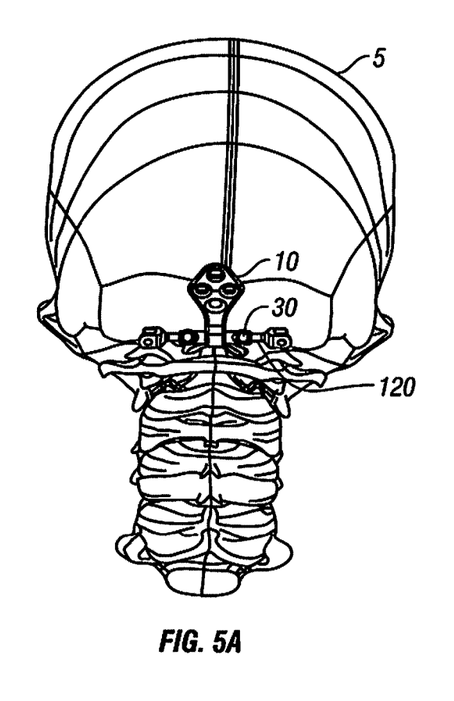
FIGS. 5A and 5B illustrate an occipital plate with alternative lateral connectors attached thereto according to some embodiments.
Figure 5B:
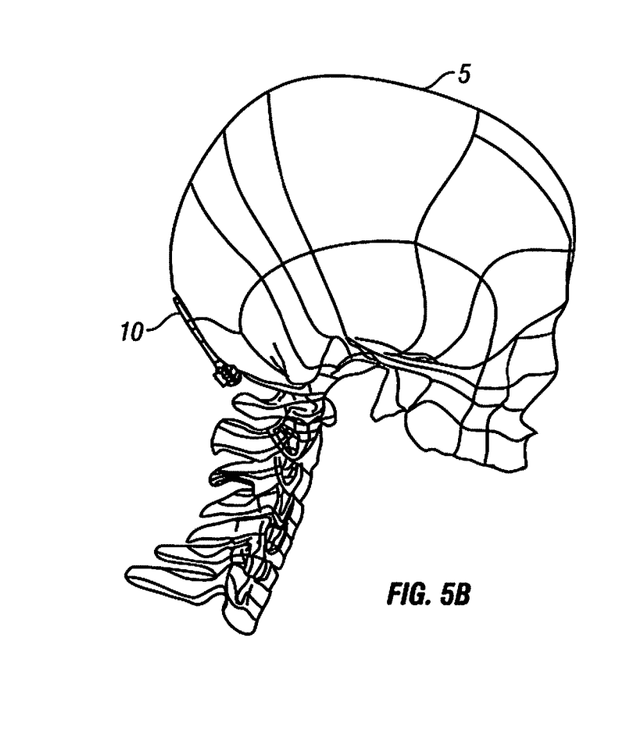

FIGS. 5A and 5B illustrate an occipital plate 10 attached to occipital bone 5, the occipital plate 10 having alternative lateral connectors 120 extending outwardly from the lateral members 30 according to some embodiments. Unlike the lateral connectors in FIGS. 4A and 4B, the lateral connectors 120 comprise straight arms having polyaxial screw head receivers 112 placed thereon. The polyaxial screw head receivers 112 are configured to receive one or more stabilization rods that extend up into the skull region, thereby providing a means for rod stabilization.

Figure 6A:
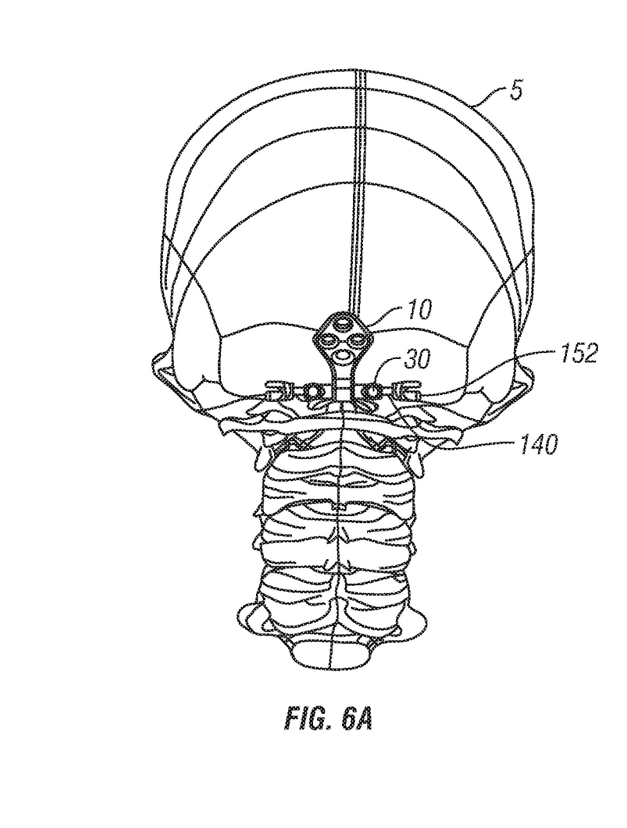
FIGS. 6A and 6B illustrate an occipital plate with alternative lateral connectors attached thereto according to some embodiments.
Figure 6B:
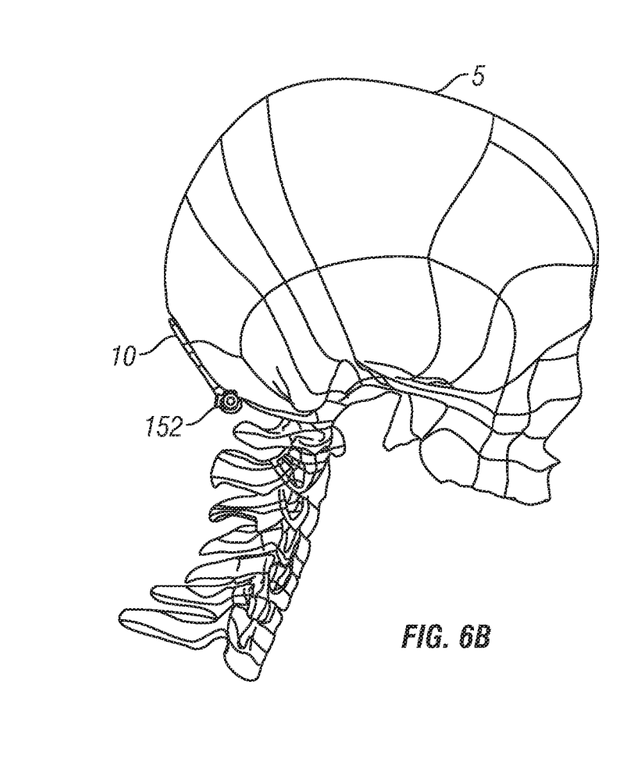

FIGS. 6A and 6B illustrate an occipital plate 10 attached to occipital bone 5, the occipital plate 10 having alternative lateral connectors 140 extending outwardly from the lateral members 30 according to some embodiments. The lateral connectors 140 comprise straight arms having polyaxial screw head receivers 152 placed thereon. Compared to the system in FIGS. 5A and 5B, the polyaxial screw head receivers 152 have a different orientation, and thus, are capable of receiving one or more stabilization rods at a different angle.

As shown in FIGS. 4A-6B, a number of different lateral connectors can extend from lateral members 30. One or more polyaxial screw head receivers can be attached to the lateral connectors and can have different orientations for receiving stabilization rods. In some embodiments, once the lateral connectors are positioned and oriented in a desired position relative to the lateral members, the lateral connectors can be secured in place via one or more locking mechanisms, such as a set screw. While in FIGS. 4A-6B, the various lateral connectors are oriented such that there is symmetry across a mid-line of the occipital plate, in other embodiments, lateral connectors on opposite sides of a plate can have different orientations to more specifically accommodate a patient's anatomy.

Additional occipital plate systems are now described that utilize a clamping technology to secure the system to sub-occipital levels. Instead of or in addition to using screws and hooks to secure the system to vertebrae at sub-occipital levels, the present system utilizes a number of clamping arms that can be secured to vertebral bodies. One or more cables can be provided that extend through the clamping arms to add fixation and stability to the system. By using clamping arms and optional cables to secure the system to vertebrae, this advantageously provides a low profile system that in some instances, may be less than conventional screw and hook based systems.

Figure 7A:
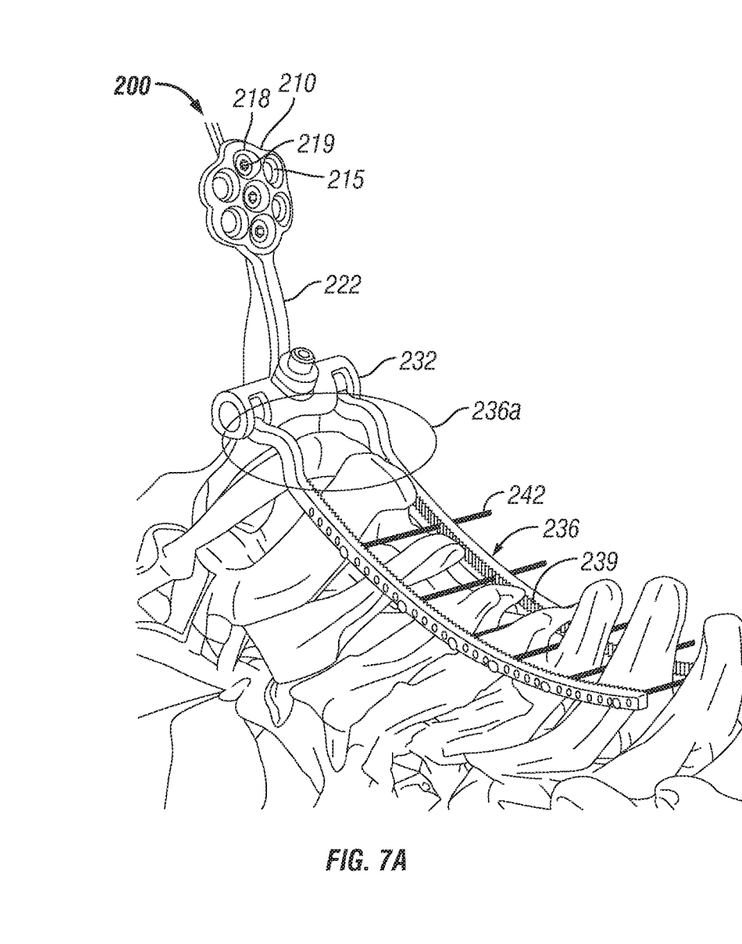
FIGS. 7A and 7B illustrate a novel occipital plate system using clamping arms according to some embodiments.
Figure 7B:
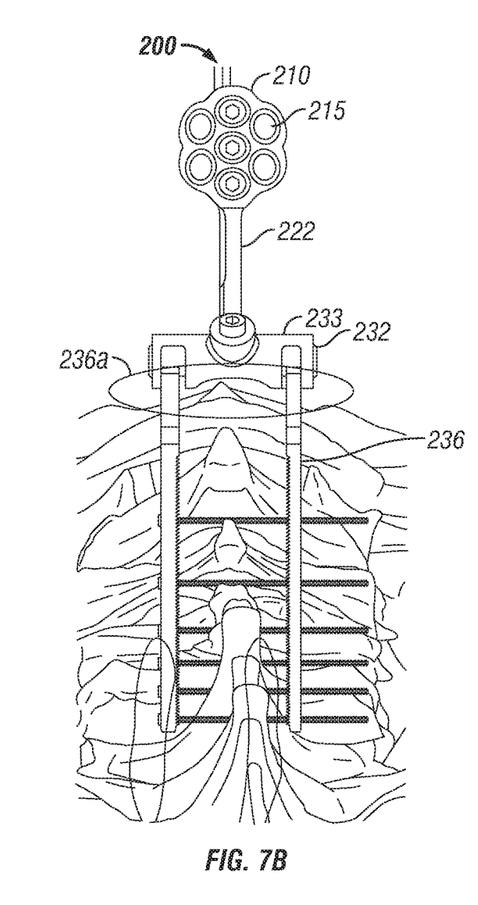

FIGS. 7A and 7B illustrate a novel occipital plate system using clamping arms according to some embodiments. The occipital plate system 200 comprises an occipital plate 210, an extension member 222, an articulating joint member 232 and clamping arms 236 extending therefrom. The clamping arms 236 include a plurality of teeth 237 (shown in FIG. 11) that allow the clamping arms 236 to grip against bone (e.g., the lamina) when tensioning cables 242 are inserted and tensioned through the clamping arms 236.

The occipital plate 210, which can attach to an occipital bone, includes a plurality of apertures 215 for receiving one or more fasteners to secure the plate 210 to bone. In some embodiments, the apertures 215 are configured such that one or more fasteners are positioned in an inion of the skull, which is a ridge of cortical bone that runs along the medial axis of the occipital bone. The inion advantageously provides the fasteners with a high amount of purchase and bone for fixation, thereby helping to secure the system. A number of mid-apertures 218 can also be positioned near a middle section of the plate 210. These mid-apertures 218 can receive one or more fasteners 219 (e.g., locking screws) that can extend through holes in the extension member 222, thereby securing the occipital plate 210 and extension member 222 to bone. In some embodiments, the occipital plate 210 is pre-contoured to match the natural curve of the occipital bone.

The extension member 222 comprises a connecting arm that extends from the occipital plate 210 to a sub-occipital joint member 232. While in some embodiments, the extension member 222 can be attached to the occipital plate 210 via fasteners 219 (as discussed above), in other embodiments, the extension member 222 is operably attached to a bottom portion of the occipital plate 210 from it extends. Like the occipital plate 210, the extension member 222 can be curved. In some embodiments, the extension member 222 can be curved to keep the profile of the articulating joint member 232 within a normal protrusion height of the spinous process.

Figure 8:
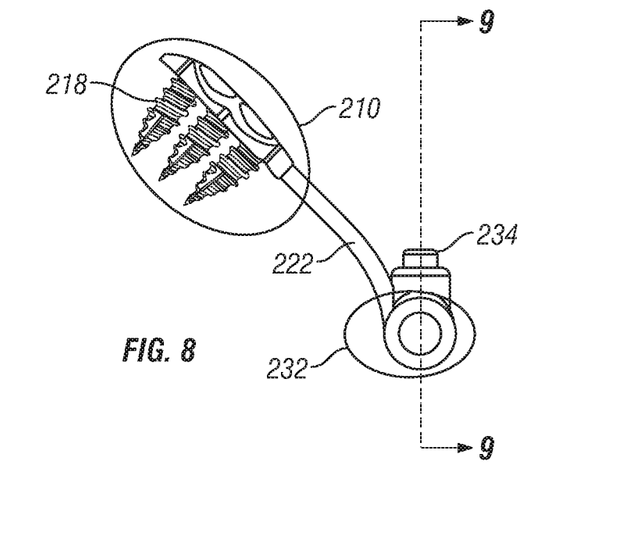
FIG. 8 is a side view of an occipital plate and articulating joint member of an occipital plate system according to some embodiments.
Figure 9:
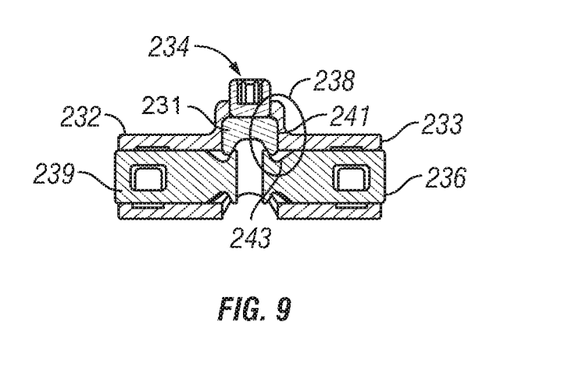
FIG. 9 is a back view of an articulating joint member of an occipital plate system according to some embodiments.
Figure 10A:
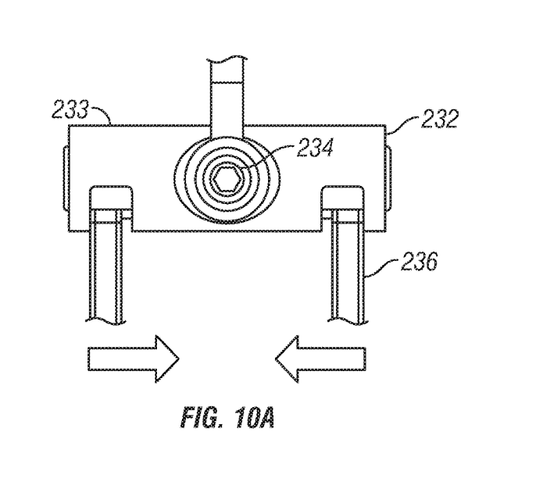
FIGS. 10A and 10B are different top views of an articulating joint member of an occipital plate system according to some embodiments.
Figure 10B:
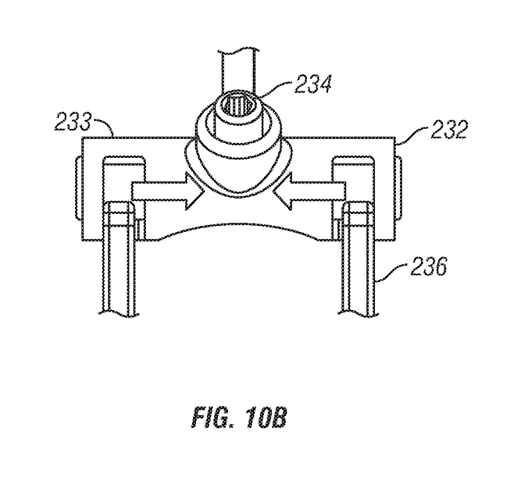

The extension member 222 attaches to the articulating joint member 232 as shown in FIG. 8. The articulating joint member 232, which is shown in FIGS. 9, 10A and 10B, comprises a housing 233 from which a pair of attached clamping arms 236 extend. In some embodiments, the articulating joint member 232 can articulate relative to the clamping arms 236 prior to locking the articulating joint member 232 in place. With reference to FIG. 9, the articulating joint member 232 further includes a set screw 234 that is operably attached to a locking wedge 231. As shown in area 238, the bottom of the locking wedge 231 has a pair of tapers 241 that can engage tapered portions 243 formed in the clamping arms 236. When the set screw 234 is downwardly rotated into the locking wedge 231, the tapers 241 of the locking wedge 231 engage the tapered portions 243 of the clamping arms 236, thereby drawing the clamping arms 236 medially together against the housing 233, which locks the clamping arms 236 into position. The medial direction in which the clamping arms 236 move is shown in FIGS. 10A and 10B. As the clamping arms 236 are moved medially towards each other, inner surfaces of the clamping arms 236 press against vertebral bone (e.g, lamina), thereby securing the occipital plate system to sub-occipital vertebral members.

Figure 11:
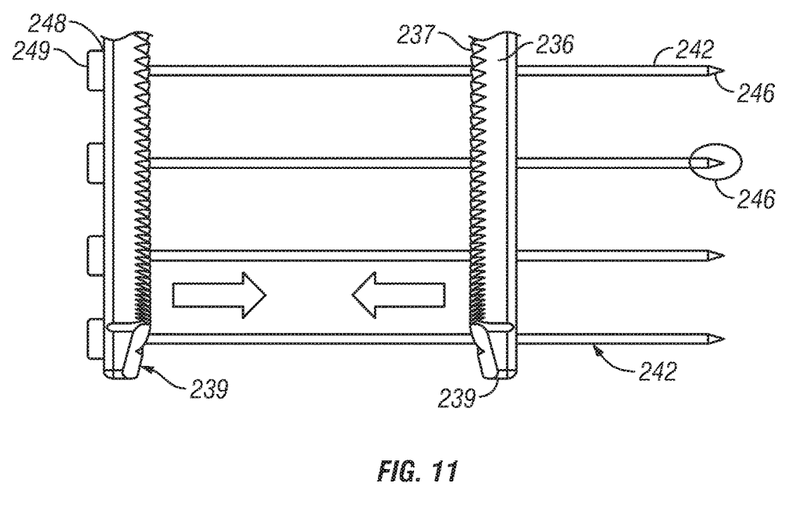
FIG. 11 is a top view of clamping arms of an occipital plate system according to some embodiments.

FIG. 11 is a top view of clamping arms of the occipital plate system according to some embodiments. The clamping arms 236 comprise a plurality of teeth 237 that extend along inner surfaces thereof. The teeth 237 advantageously allow the arms 236 to grip onto vertebral bone as the arms 236 are moved medially inward toward each other via rotation of the set screw 234. In some embodiments, the teeth 237 can be saw-tooth shaped, while in other embodiments, the teeth 237 are not saw-toothed. In some embodiments, rather than having teeth 237, a plurality of surface roughening features, such as ridge-members, can be provided along a length of the clamping arms 236.

The clamping arms 236 have a number of features that can better accommodate a natural human anatomy. For example, as shown in FIG. 7A, the clamping arms 236 can have an upper curved portion 236a in order to avoid the lateral portions of the C1 posterior arch. Moreover, as shown in FIG. 11, in some embodiments, the clamping arms 236 have a lowered tapered section 239 that advantageously matches a spinous process/lamina transition portion along the vertebrae, thereby better accommodating the natural anatomy of a patient.

In some embodiments, each of the clamping arms 236 can include a plurality of incremental holes 248 that extend along a length of the arms. The holes 248 are configured to receive one or more tension cables 242 that are used with the clamping arms 236 to gain fixation and stability.

The tension cables 242, shown in FIG. 11, comprise flexible members that extend through the clamping arms 236. On their proximal end, the tension cables 242 include a clamping flange 249 that rests against a surface of a clamping arm 236, thereby allowing the cable to be placed in tension when it is pulled against the surface of the clamping arm. On their distal end, the tension cables 242 can include a sharp penetration end that advantageously allows penetration through an interspinous ligament or a spinous process. One or more cables 242 can be placed intermittently along a length of the clamping arms 236 and placed in tension, thereby stabilizing and locking the clamping arms 236 to the vertebral bodies. Advantageously, as shown in FIG. 7A, the combined clamping arms 236 and tension cables 242 maintain a low-profile. In some embodiments, the clamping arms 236 and tension cables 242 maintain a profile that is below an upper surface of a majority of, if not all, of the vertebrae which they pass.

While the occipital plate system in FIGS. 7A-11 use an occipital plate 210, one skilled in the art will appreciate that alternate occipital plates can be provided. For example, the occipital plate 10 shown in FIG. 1 having lateral members 30 can be used instead. The extension member 222 could extend from a bottom portion of the occipital plate 10 and connect to an articulating joint member having a housing as discussed above.

One skilled in the art will appreciate the number of advantages provided by the occipital plate systems discussed above. Among the advantages include greater adjustability and flexibility, as well as a low profile.

While the invention herein disclosed has been described by means of specific embodiments and applications thereof, numerous modifications and variations can be made thereto by those skilled in the art without departing from the scope of the invention.

What is claimed is:

1. An occipital plate system comprising:
an occipital plate comprising a body having a diamond-shaped upper portion and a lower portion extending from the upper portion, the lower portion including an opening;
a lateral member received through the opening, the lateral member including a top aperture having a longitudinal axis that is at an angle relative to a longitudinal axis of the occipital plate, and the lateral member including a side aperture;
a rod accepting component having a top opening and being received in the top aperture; and
a lateral connector configured to be received in the top opening or the side aperture,
wherein the lateral member is rotatable and translatable such that the lateral member is adjustable relative to the occipital plate, and
wherein the rod accepting component includes a polyaxial screw head receiver, and the lateral connector comprises an uncurved arm attached to the polyaxial screw head receiver positioned in the top aperture in the lateral member.

2. The system of claim 1, wherein the occipital plate is tapered such that it has a thickness that is greater near the lower portion of the plate.

3. The system of claim 1, wherein the upper portion of the plate includes a plurality of holes configured to receive one or more fasteners.

4. The system of claim 3, wherein the holes are arranged in a diamond-shaped pattern.

5. The system of claim 1, wherein the lateral member extends from a first end to a second end, and the side aperture for receiving the lateral connector is positioned at the first end or the second end.

6. The system of claim 1, wherein the lateral member extends from a first end to a second end along a longitudinal axis, and the side aperture is aligned along the longitudinal axis.

7. An occipital plate system comprising:
an occipital plate comprising a body having a diamond-shaped upper portion and a lower portion extending from the upper portion, the lower portion including an opening;

a lateral member received through the opening, the lateral member extending from a first end to a second end, the lateral member including a first top aperture proximate the first end and a second top aperture proximate the second end, the first top aperture having a longitudinal axis that is at an angle relative to a longitudinal axis of the occipital plate, and the lateral member including a first side aperture at the first end, and a second side aperture at the second end; and a rod accepting component received in each of the first and second top apertures, which are each configured to secure a lateral connector thereto, wherein the lateral member is rotatable and translatable such that the lateral member is adjustable relative to the occipital plate, and wherein the rod accepting components each include a polyaxial screw head receiver, and the lateral connector comprises a curved arm attached to a polyaxial screw head receiver positioned in the top aperture in the lateral member.

8. The system of claim 7, wherein the occipital plate is tapered such that it has a thickness that is greater near the lower portion of the plate.

9. The system of claim 7, wherein the upper portion of the plate includes a plurality of holes.

10. The system of claim 9, wherein the holes are arranged in a diamond-shaped pattern.

11. An occipital plate system comprising:

an occipital plate comprising a body having a diamond-shaped upper portion and a lower portion extending from the upper portion, the upper portion including at least three holes and the lower portion including an opening;

at least three fasteners, each fastener extending through each hole of the at least three holes of the occipital plate;

a lateral member received through the opening, the lateral member extending from a first end to a second end, the lateral member including a first top aperture proximate the first end and a second top aperture proximate the second end, the first and second top apertures each having a longitudinal axis that is at an angle relative to a longitudinal axis of the occipital plate, and the lateral member including a first side aperture at the first end and a second side aperture at the second end;

a rod accepting component received in each of the first and second top apertures, respectively; and a lateral connector coupled to each of the rod accepting components or to the first and second side apertures, wherein the rod accepting component includes a polyaxial screw head receiver, and the lateral connector comprises an arm attached to the polyaxial screw head receiver positioned in the top aperture in the lateral member.

12. The system of claim 11 wherein the occipital plate is tapered such that it has a thickness that is greater near the lower portion of the plate.

13. The system of claim 11, wherein the lateral member is rotatable and translatable such that the lateral member is adjustable relative to the occipital plate.

\* \* \* \* \*